(12) United States Patent
Al-Sabawi et al.

(10) Patent No.: US 10,746,659 B2
(45) Date of Patent: Aug. 18, 2020

(54) DETERMINATION OF ORGANIC SILICON IN HYDROCARBONACEOUS STREAMS

(71) Applicant: ExxonMobil Research and Engineering Company, Annandale, NJ (US)

(72) Inventors: Mustafa Al-Sabawi, London (CA); Lindsay A. Mitchell, Wyoming (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 128 days.

(21) Appl. No.: 16/021,558

(22) Filed: Jun. 28, 2018

(65) Prior Publication Data

US 2019/0025220 A1    Jan. 24, 2019

Related U.S. Application Data

(60) Provisional application No. 62/535,446, filed on Jul. 21, 2017.

(51) Int. Cl.
*G01N 21/73* (2006.01)
*G01N 33/22* (2006.01)
(Continued)

(52) U.S. Cl.
CPC .......... *G01N 21/73* (2013.01); *G01N 1/4055* (2013.01); *G01N 1/4077* (2013.01); *G01N 33/22* (2013.01);
(Continued)

(58) Field of Classification Search
CPC .... G01N 21/73; G01N 21/714; G01N 1/4077; G01N 33/28; G01N 33/22;
(Continued)

(56) References Cited

U.S. PATENT DOCUMENTS 5,259,254 A * 11/1993 Zhu .................. H01J 49/04
239/102.2
8,908,827 B2    12/2014 Carnahan et al.
(Continued)

OTHER PUBLICATIONS

P. D. Goulden, "Modified Ultrasonic Nebulizer for Inductively Coupled Argon Plasma Atomic Emission Spectrometry", Anal. Chem. 1984 (Year: 1984).*

*Primary Examiner* — Maurice C Smith
(74) *Attorney, Agent, or Firm* — Glenn T. Barrett

(57) ABSTRACT

Systems and methods are provided for determining the organic silicon content of petroleum fractions, such as refinery fractions. This can be achieved in part based on performing solvent-enhanced selective filtration on a hydrocarbonaceous sample to substantially remove inorganic silicon from the sample while retaining at least a substantial portion of the organic silicon in the sample. After the solvent-enhanced selective filtration, the organic silicon content of the filtered sample can be determined. The ability to determine the organic silicon content of a sample can be used to identify crude fractions and/or refinery fractions that may cause contamination problems within a refinery while reducing or minimizing the occurrence of false positive tests that could result from detection of inorganic silicon.

17 Claims, 1 Drawing Sheet

(51) Int. Cl.
*H01J 49/00* (2006.01)
*G01N 1/40* (2006.01)
*H01J 49/10* (2006.01)
*H01J 49/34* (2006.01)

(52) U.S. Cl.
CPC ........ *H01J 49/0027* (2013.01); *H01J 49/105* (2013.01); *H01J 49/34* (2013.01); *G01N 2001/4061* (2013.01); *G01N 2001/4088* (2013.01)

(58) Field of Classification Search
CPC ............ G01N 2001/4061; G01N 30/72; H01J 49/0027; H01J 49/105; G01J 3/443
See application file for complete search history.

(56) References Cited

U.S. PATENT DOCUMENTS

| | | | |
|---|---|---|---|
| 9,133,403 B2* | 9/2015 | Mezza | C10G 67/04 |
| 2008/0085231 A1* | 4/2008 | Vitse | B01D 53/9409 |
| | | | 423/239.1 |
| 2013/0288885 A1* | 10/2013 | Domokos | B01J 29/7461 |
| | | | 502/77 |
| 2014/0165831 A1* | 6/2014 | Taylor | C10G 25/12 |
| | | | 95/107 |
| 2015/0235827 A1* | 8/2015 | Bazargan | H01J 49/0031 |
| | | | 702/116 |
| 2016/0135277 A1* | 5/2016 | Duimstra | H05H 1/30 |
| | | | 356/316 |
| 2016/0137931 A1* | 5/2016 | Kumar | C10G 47/34 |
| | | | 208/92 |
| 2017/0305812 A1* | 10/2017 | Keusenkothen | C10G 35/085 |

* cited by examiner

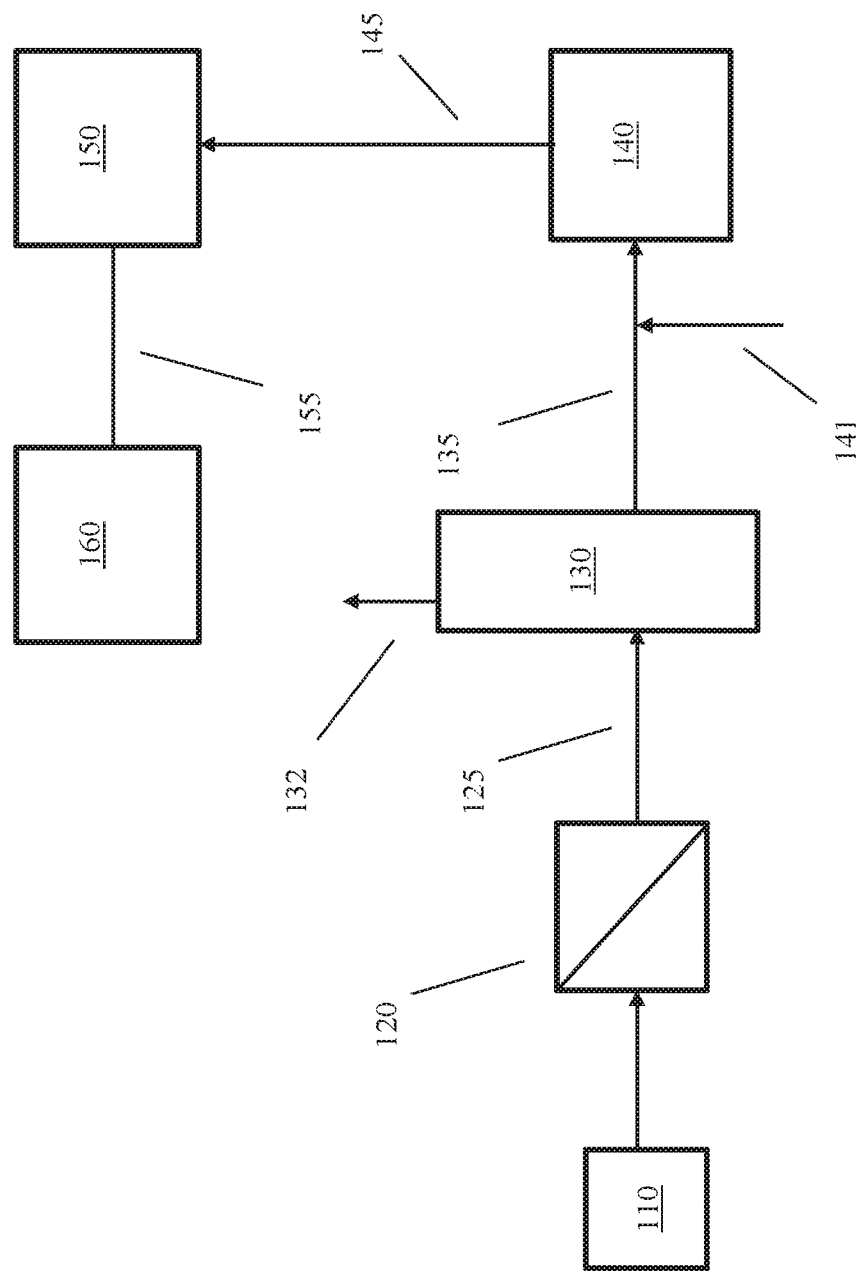

DETERMINATION OF ORGANIC SILICON IN HYDROCARBONACEOUS STREAMS

CROSS-REFERENCE TO RELATED APPLICATIONS

This Application Claims the Benefit of U.S. Provisional Application No. 62/535,446, Filed on Jul. 21, 2017, the Entire Contents of which are Incorporated Herein by Reference

FIELD

This invention relates to systems and methods for characterizing the silicon content of crude fractions and refinery fractions.

BACKGROUND

Chemical additives are often utilized in crude oil production to increase resource recovery and optimize the handling and delivery of crude oil. Various types of chemicals are required to aid the production, handling and transportation of crude oil. These chemicals may contaminate/remain in the crude oil as impurities (in trace amounts) from production until the crude reaches the refinery. In addition to oil production, such chemicals are also used in refinery units (e.g. delayed cokers) to control foaming issues.

The presence of such silicon compounds in a crude fraction or refinery fraction can create difficulties for a variety of types of processes within a refinery setting. For example, silicon is a known poison for various types of catalysts. As a result, the ability to reliably detect the presence of silicon with a crude fraction or refinery fraction can be beneficial, to reduce or minimize undesirable contamination of catalysts and/or other refinery equipment.

U.S. Pat. No. 8,908,827 describes methods for detecting silicon in a petroleum fraction using X-ray fluorescence. The methods include use of standard solutions containing organosiloxanes in an amount of 0.5 wt % to 3.5 wt % as reference samples for the determination of silicon content in fuels boiling range petroleum fractions having comparable amounts of silicon content.

SUMMARY

In an aspect, a method is provided for determining the silicon content of a hydrocarbonaceous sample. The method can include mixing a hydrocarbonaceous sample with an aromatic solvent to form a mixture. The hydrocarbonaceous sample can correspond to a hydrocarbon sample, or the hydrocarbonaceous sample can include compounds containing heteroatoms typically found in crude and/or refinery fractions. The mixture can include about 20 wt % to about 80 wt % of an aromatic solvent relative to a weight of the mixture. A solids removal process, such as filtration, can then be performed on the mixture. The solids removal process can be suitable for removing particles having a particle size of about 1.0 μm or larger to form a reduced solids mixture. The silicon content of the hydrocarbonaceous sample can then be characterized using a detection method comprising inductively coupled plasma, such as inductively coupled plasma atomic emission spectrometry. The characterization can be performed based on removal of at least a portion of the aromatic solvent from the reduced solids mixture prior to characterization; based on characterization of the reduced solids mixture and then determining the silicon content based the relative weight of aromatic solvent and hydrocarbonaceous sample; or a combination thereof.

In some aspects, about 15 wt % or more of the silicon content in the mixture prior to solids removal can correspond to inorganic silicon. In some aspects, about 10 wt % or less of the silicon content in the reduced solids mixture (after solids removal) can correspond to inorganic silicon, or about 5 wt % or less.

In some aspects, the aromatic solvent can include 50 wt % or more of 1-ring aromatic hydrocarbons, such as benzene, toluene, and/or xylene. In some aspects, the aromatic solvent can correspond to a naphtha boiling range fraction having an aromatics content of about 20 wt % or more. In such an aspect, the aromatics content of the naphtha boiling range fraction can optionally include aromatics containing heteroatoms, aromatics containing 2 or more aromatic rings, or a combination thereof. In such an aspect, the naphtha boiling range fraction can optionally include a 1-ring aromatic hydrocarbon content of about 20 wt % or more (or about 25 wt % or more, or about 30 wt % or more).

In some aspects, the hydrocarbonaceous sample can correspond to a sample derived from a crude fraction, a refinery fraction, or a combination thereof. Optionally, a refinery fraction can correspond to a fraction that is at least in part bio-derived.

In an aspect, system for characterizing a silicon content of a hydrocarbonaceous sample is provided. The system can include a sample volume in fluid communication with a filter having a pore size of less than 1.0 μm. The system can further include a nebulizer comprising a nebulizer inlet and a nebulizer outlet, the nebulizer inlet being in fluid communication with the permeate side of the filter. The system can further include a plasma chamber comprising an inductively coupled argon plasma, the plasma chamber being in fluid communication with the nebulizer outlet. The system can further include an atomic emission spectrometer coupled to the plasma chamber. Optionally, the system can further include a boiling point separator, where a separator inlet is in fluid communication with the sample volume and a separator outlet is in fluid communication with the filter. Such a boiling point separator can optionally correspond to at least one of a flash separator and a distillation column.

BRIEF DESCRIPTION OF THE DRAWINGS

FIG. 1 shows an example of a system for performing silicon detection using inductively coupled plasma atomic emission spectrometry.

DETAILED DESCRIPTION OF THE EMBODIMENTS

Overview

In various aspects, systems and methods are provided for determining the organic silicon content of petroleum fractions, such as refinery fractions. This can be achieved in part based on performing solvent-enhanced selective filtration on a petroleum sample (or other hydrocarbonaceous sample) to substantially remove inorganic silicon from the sample while retaining at least a substantial portion of the organic silicon in the sample, such as up to all or substantially all of the organic silicon. After the solvent-enhanced selective filtration, the organic silicon content of the filtered sample can be determined. The organic silicon content can be determined using a characterization technique that involves an inductively coupled plasma, such as inductively coupled plasma atomic emission spectrometry (ICP-AES). The ability to determine the organic silicon content of a sample can be used to identify crude fractions and/or refinery fractions that may cause contamination problems within a refinery while reducing or minimizing the occurrence of false positive tests that could result from detection of inorganic silicon.

Foaming problems occur in many oilfield processes, such as extraction processes for production of tight oil and production of bitumen from oil sands. Anti-foaming agents are commonly used to mitigate such problems. These agents, which are typically oil-soluble silicon-based chemicals such as polydimethylsiloxane (PDMS), can pose a variety of problems for refiners when present in a crude oil fraction. For example, silicon can degrade the quality of refinery products such as gasoline and distillates. Additionally, silicon is a known poison for catalysts in refinery reactors/units. More generally, silicon-containing compounds can generally present similar problems to those presented by anti-foaming agents.

While refinery desalter technology may remove portions of these (organic) silicon-based chemicals, analysis of desalted crude samples has shown that much of the silicon can still remain in a crude fraction. Unfortunately, after entering a refinery, such organic silicon-based chemicals can start to decompose at temperatures of 300° C.-350° C. Such temperatures are commonly encountered in various types of refinery equipment, such as refinery furnaces, crude towers, and cokers, which can lead to decomposition of organosilicon polymers (such as polydimethylsiloxane) into gasoline and distillate boiling range organosilicon products. The resulting organosilicon decomposition products can then be distributed across a wide range of refinery streams, becoming a threat to catalysts and finished products.

Some conventional analytical methods that can be utilized to quantify the amount of organic silicon in hydrocarbons. While X-ray fluorescence can be used, the detection limit of this technique limits the suitability of X-ray fluorescence to samples containing ~1 wt % of silicon or more. By contrast, silicon levels corresponding to a few parts per million by weight can potentially be harmful in a refinery setting.

Inductively coupled plasma atomic emission spectrometry (ICP-AES) provides an option for a technique that can measure the amount of elemental silicon in hydrocarbon samples in ppm levels. The challenge of ICP-AES, however, is that fine particles/solids (<10 microns) that may be present in the sample can impact the measurement due to potential solid carryover with the argon gas/kerosene mist mixture during analysis. These inorganic solids can contain silicon which would consequently contribute to the amount of silicon measured by the ICP method. For example, crude oil fractions derived from tar sands or oil sands can include silica-containing particles that can be carried with the mist mixture during analysis. Hence, the total amount of silicon detected would be the sum of organic and inorganic silicon in the sample. This can present difficulties, since inorganic silicon (such as sand particles) is less likely than organic silicon to present the same difficulties with regard to catalyst poisoning/equipment contamination. In other words, understanding the nature of the silicon present within a crude fraction or refinery fraction can also be valuable in determining whether a fraction is suitable for introduction into a refinery process.

To be able to decouple organic silicon from inorganic silicon, one approach would be to remove the solids from the hydrocarbon sample by conventional methods, including filtration and/or centrifugation. While filtration is likely not practical in a commercial setting, for laboratory scale characterization of a sample, filtration can allow for removal of inorganic particles. Unfortunately, it has been observed that silicon-based anti-foam based additives are partially/not completely soluble in crudes and refinery streams. As a result, it has been discovered that filtration tends to also remove most, if not substantially all, of the organic silicon present in the sample.

It has been discovered that the problems with attempting to selectively remove inorganic silicon from a sample using filtration can be at least partially overcome by adding an aromatic solvent to the sample prior to filtration. For example, an aromatic solvent such as benzene, toluene, or xylene can be added to the sample to solubilize the anti-foam additive (or other organic silicon-containing compounds) in the sample and/or to prevent adsorption of the organic silicon-containing compounds on solid particles that may be present. Conventional solids removal methods may then be employed to remove particulates from the sample. Addition of a suitable amount of aromatic solvent followed by filtration (or another conventional solids removal method, such as centrifugation) can reduce or minimize the presence of inorganic silicon from the sample by reducing the content of particles having an average particle size of greater than a threshold amount, such as particles having an average particle size greater than 1 μm. This can allow ICP-AES to be used to characterize the organic silicon content of a sample while reducing or minimizing the risk of over-estimation of the amount of organic silicon that is present. If desired, evaporation or extraction of the added solvent can be carried out in the final step before utilizing elemental measurement techniques, such as ICP-AES, to determine the total amount of organic (soluble) silicon in the sample. Sample/solvent mass accounting can allow for the accurate determination of silicon concentration in cases where a portion of the sample (i.e. light ends) is lost during the solvent removal step and/or in cases where at least a portion of the solvent remains in the sample during characterization. It is noted that the methods described herein can also be effective for improving silicon detection using other methods based on inductively coupled plasma, such as inductively coupled plasma—mass spectrometry (ICP-MS).

Definitions

In this discussion, a crude fraction can refer to any portion of a crude oil, up to and including a whole crude. A crude fraction can also refer to a synthetic crude or crude fraction. In this discussion, a refinery fraction can correspond to any type of feed and/or effluent that may be encountered in a conventional petroleum processing environment and/or chemical plant environment. Thus, a refinery fraction could refer to a feed to or effluent from hydroprocessing, thermal processing (e.g., coking, steam cracking), distillation and separation, reforming, alkylation, oligomerization, aromatic formation, and/or other conversion processes typically performed using petroleum/hydrocarbonaceous feeds. Refinery fractions can also include effluents that correspond (at least in part) to a bio-derived sample, such as a gasoline fraction that includes bio-derived ethanol.

In this discussion, the term "hydrocarbon" is used in the conventional sense to refer to a compound containing only carbon and hydrogen atoms. The term "hydrocarbonaceous" can be used to refer to compounds, mixtures, and/or other fractions that are substantially composed of hydrocarbons or hydrocarbon-like compounds, but that may also include heteroatoms (i.e., not carbon or hydrogen), such as heteroatoms typically found in petroleum fractions, crude fractions, and/or refinery fractions. Examples of such heteroatoms include sulfur, nitrogen, and various trace metals such as Ni, V, and Fe. For a mixture or fraction, the combined carbon and hydrogen content of a hydrocarbonaceous mixture or fraction can correspond to at least 85 wt % of the total weight of the mixture or fraction, or at least 90 wt %, or at least 95 wt %, or at least 98 wt %, such as up to 100 wt % (i.e., a hydrocarbon mixture or fraction is included within the definition for a hydrocarbonaceous fraction). It is noted that a hydrocarbonaceous sample can correspond to a portion of one or more hydrocarbonaceous compounds, mixtures, and/or fractions.

In this discussion, inorganic silicon refers to silicon present in a sample where the silicon-containing compound or material does not include any silicon-carbon bonds. As an example, polydimethylsiloxane is considered to be organic silicon, since the silicon atoms in polymethylsiloxane include two silicon-carbon bonds as well as two silicon-oxygen bonds.

In this discussion, unless otherwise specified, detection of the amount of silicon in a sample corresponds to detection of silicon using inductively coupled plasma atomic emission spectrometry (ICP-AES) according to ASTM D5185. Although the text of ASTM D5185 states that the method is suitable for lubricant base oils, the methodology described in ASTM D5185 can be applied more generally to crude and/or refinery fractions having a wide variety of boiling ranges. It is noted that ASTM D7111 and ASTM D7691 provide additional test methods based on ICP-AES for detection of elements such as silicon in middle distillates and crude oils, respectively. To the degree that the boiling range of a sample causes the method of ASTM D5185 to be inoperative, the methods of ASTM D7111 or ASTM D7691 may be substituted.

In this discussion, the particle size of a particle is defined as the diameter of the smallest bounding sphere that can contain the particle.

Samples for Characterization

One way of defining a feedstock is based on the boiling range of the feed. One option for defining a boiling range is to use an initial boiling point for a feed and/or a final boiling point for a feed. Another option, which in some instances may provide a more representative description of a feed, is to characterize a feed based on the amount of the feed that boils at one or more temperatures. For example, a "T5" boiling point for a feed is defined as the temperature at which 5 wt % of the feed will boil off. Similarly, a "T95" boiling point is a temperature at 95 wt % of the feed will boil. A suitable ASTM method can be used for characterization of boiling points (including fractional boiling points), such as ASTM D2887.

Samples suitable for characterization of silicon content can correspond to any convenient type of crude fraction or refinery stream. Thus, the methods described herein can be used for characterization of a wide range of petroleum and chemical feedstocks. Suitable feedstocks include whole and reduced petroleum crudes, dilbits from tar sands or oil sands, tight oils, other conventional and non-conventional crudes, atmospheric and vacuum residua, propane deasphalted residua, e.g., brightstock, cycle oils, FCC tower bottoms, gas oils, including vacuum gas oils and coker gas oils, naphthas, light to heavy distillates including raw virgin distillates, hydrocrackates, hydrotreated oils, slack waxes, Fischer-Tropsch waxes, raffinates, and mixtures of these materials.

In various aspects, the silicon content of a sample can include organic silicon, inorganic silicon, or a combination thereof. For samples where sufficient inorganic silicon is present to potentially interfere with characterization, the inorganic silicon content can correspond to about 10 wt % or more of the total silicon content of the sample, or about 15 wt % or more, or about 25 wt % or more, or about 40 wt % or more, such as up to substantially all of the silicon in the sample. A sample where substantially all of the silicon in the sample is inorganic silicon can correspond to a sample where up to 90 wt % of the silicon is inorganic, or up to 98 wt %, or up to 100 wt %. After removal of solid particles, the amount of inorganic silicon in the sample (or the mixture of sample and aromatic solvent) can correspond to 10 wt % or less of the silicon, or 5.0 wt % or less, or 1.0 wt % or less, such as down to substantially no inorganic silicon content.

Prior to characterization, a sample can be mixed with an aromatic solvent to improve the solubility of organosilicon compounds in the sample. Suitable aromatic solvents can include 1-ring aromatic hydrocarbons, such as benzene, toluene, xylene, and other alkyl-substituted benzenes. In some aspects, the aromatic solvent can correspond to a portion of a naphtha boiling range fraction. In such aspects, the naphtha boiling range fraction can be added to the hydrocarbonaceous fraction to form the mixture. In such aspects, the naphtha boiling range fraction can comprise about 20 wt % aromatics or more, or about 25 wt % aromatics or more, or about 30 wt % aromatics or more, or about 35 wt % aromatics or more, such as up to 50 wt % aromatics or possibly still higher. In aspects where at least a portion of an aromatic solvent corresponds to a naphtha boiling range fraction, the naphtha boiling range fraction can optionally include 20 wt % or more of 1-ring aromatic hydrocarbons, or 25 wt % or more, or 30 wt % or more. In yet other aspects, at least one naphtha boiling range fraction and at least one aromatic solvent can be added to a hydrocarbonaceous fraction to form a mixture.

In this discussion, the term "aromatic solvent" is defined to include a) 1-ring aromatic hydrocarbons; b) mixtures of 1-ring aromatic hydrocarbons; c) mixtures that include more than 50 wt % of 1-ring aromatic hydrocarbons (such as 50 wt % or more of benzene, toluene, and/or xylene), or 70 wt % or more, or 90 wt % or more; d) 2-ring aromatic hydrocarbons (such as naphthalene) and e) naphtha boiling range fractions that include 20 wt % aromatics or more, or 25 wt % aromatics or more, or 30 wt % aromatics or more. In some aspects, the aromatics can include aromatics that contain heteroatoms, such as furan or pyridine. In some aspects, the aromatics can correspond to hydrocarbons.

The amount of aromatic solvent added to a sample can be sufficient to allow for substantially complete solubilization of organosilicon compounds within a sample. This can correspond to adding 20 wt % to 80 wt % of aromatic solvent to a sample, relative to the total weight of the mixture. Additionally or alternately, in aspects where a naphtha boiling range fraction is added to the hydrocarbonaceous fraction to form the mixture, the amount of naphtha boiling range fraction added to the mixture can correspond to 20 wt % to 80 wt % of the mixture. Due to the substantial amount of aromatic solvent, it can be convenient to remove the aromatic solvent from the sample after filtration and prior to characterization of the silicon content. This can result in loss of portions of the sample that have a similar distillation point (or lower) relative to the aromatic solvent. This loss can be accounted for based on the difference in the weight of the sample prior to addition of the solvent and after solvent removal.

After adding an aromatic solvent to a sample for characterization, solid particle removal can be performed on the combined solvent and sample. The particle removal can be performed by any convenient method. One example of solid particle removal can be filtration. A filter can be used that is suitable for removal of particles having an average particle size of greater than about 1.0 micron from the combined solvent and sample. Due to the presence of the aromatic solvent, at least a portion (such as up to substantially all) of the organic silicon present in the sample can pass through the filter into the permeate or filtrate.

After filtration, centrifugation, and/or another suitable method for separation of solids from the remaining portion of the mixture, characterization of the silicon content can be performed. In some aspects, characterization can be performed on the mixture of the hydrocarbonaceous sample plus the aromatic solvent. In other aspects, at least a portion of the aromatic solvent can be removed prior to characterization. Removal of the aromatic solvent can be performed by any convenient method, such as distillation, evaporation, flash separation, and/or extraction. Depending on the method of separation, a portion of the sample may also be removed with the aromatic solvent. For example, performing a boiling point-based separation (such as a distillation) can cause light ends and/or naphtha boiling range compounds in the sample to be removed along with the aromatic solvent. This mass loss from the sample can be accounted for by appropriate measurement of the mass of the sample before addition of the aromatic solvent and after removal of the aromatic solvent.

System Configuration

FIG. 1 shows an example of a system suitable for performing silicon detection using inductively coupled plasma atomic emission spectrometry. In FIG. 1, sample volume 110 can include a silicon-containing sample that has been mixed with an aromatic solvent. Depending on the nature of the sample, the silicon-containing sample may also include kerosene or another diluent. The sample volume can be in fluid communication with a filter 120 having a pore size of 1.0 µm or less. The sample can be passed through filter 120 to generate a permeate 125 with a reduced or minimized content of inorganic silicon. The permeate can then be optionally separated based on boiling point, such as in a flash separator or a distillation column 130, to remove at least a portion 132 of the aromatic solvent from the remaining portion 135 of the permeate. The remaining portion 135 of the permeate can then be passed into a nebulizer 140. Alternatively, the permeate side of filter 120 can be in direct fluid communication (not shown) with nebulizer 140, so that the permeate 125 is passed into the nebulizer 140. The permeate 125 or the remaining portion 135 of the permeate can be combined with an argon stream 141 prior to entering the nebulizer 140, or after entering the nebulizer housing. The nebulizer 140 can generate a mist 145 that is passed into plasma chamber 150 for exposure to the inductively coupled plasma environment. An atomic emission spectrometer 160 that is coupled to plasma chamber 150 can be used to detect the presence of silicon (and/or other desired elements).

EXAMPLES

Crude oil derived from oil sands was processed to produce a diluted bitumen crude. The diluted bitumen crude was produced without the use of an anti-foaming agent. Samples were obtained of the diluted bitumen crude from several different days of production. The samples were characterized using ICP-AES. The silicon content of the samples ranged from about 1.0 wppm to about 6.0 wppm. The silicon content corresponded to inorganic silica in the form of particles having a size of 10 µm or less. The overall particle content of the diluted bitumen crude varied, but was generally about 300 wppm.

Processing to form the diluted bitumen crude was then modified to include the use of polymethyldisiloxane (PMDS) as an anti-foaming agent. Samples were obtained of the diluted bitumen crude from several different days of production. The samples were characterized using ICP-AES both prior to filtration and after a filtration process to remove solid particles. Table 1 shows the measured silicon contents before and after the filtration. Table 1 also shows the expected organic silicon content based on the amount of PMDS used during production of the diluted bitumen crude.

TABLE 1

Silicon Content of Unfiltered and Filtered Diluted Bitumen Crude

|  | Expected Si | Si before filtration (measured) | Si after filtration (measured) |
| --- | --- | --- | --- |
| Sample 1 | 2.4 wppm | 4.9 | <1.0 |
| Sample 2 | 4.5 wppm | 8.8 | <1.0 |
| Sample 3 | 1.5 wppm | 3.8 | <1.0 |
| Sample 4 | 4.0 wppm | 5.7 | <1.0 |

As shown in Table 1, the expected organic silicon content ranges from 1.5 wppm to 4.5 wppm. The measured silicon content is higher by 1.5 wppm to 4.5 wppm due to the presence of additional inorganic silicon in the form of solid particles. Filtration is effective for removing the solid particles, but also removes the organic silicon. It is noted that 1.0 wppm corresponds to the detection limit of Si using the ICP-AES technique.

Based on the ability to remove organic silicon by filtration, it is believed that organic silicon in a petroleum sample may not be fully solvated. To test this concept, a sample of 100% toluene was spiked with PMDS. A first sample was spiked with about 2.5 wppm of PMDS, while a second sample was spiked with about 50 wppm. The samples were then characterized using ICP-AES before and after filtration. Within the limits of repeatability, the samples showed effectively the same silicon content before and after filtration (2.5 wppm vs 2.7 wppm, and 49 wppm vs 50 wppm).

In order to further investigate the ability to selectively remove inorganic silicon, additional samples were obtained of the diluted bitumen crude that was produced without the use of the PMDS anti-foaming agent. The additional samples were first characterized as is. The samples were then spiked with PMDS. The spiked additional samples were characterized before filtration, and after mixing with an equal weight of toluene, filtration, and removal of the toluene. Table 2 shows the results from the three characterizations.

TABLE 2

Selective Removal of Inorganic Silicon

|  | Si content of Diluted Bitumen Crude (no PMDS) | Si content after spiking with PMDS, unfiltered | Si content after spiking with PMDS, toluene addition, and filtration |
| --- | --- | --- | --- |
| Sample 5 | 1.6 wppm | 8.9 | 7.2 |
| Sample 6 | 2.1 wppm | 11.5 | 9.1 |

As shown in Table 2, the combination of toluene addition and filtration resulted in removal of an amount of silicon roughly corresponding to the amount of inorganic silicon, to within the detection limit of the ICP-AES technique.

ADDITIONAL EMBODIMENTS

Embodiment 1

A method for determining the silicon content of a hydrocarbonaceous sample, comprising: mixing a hydrocarbonaceous sample with an aromatic solvent to form a mixture, the mixture comprising about 20 wt % to about 80 wt % of an aromatic solvent relative to a weight of the mixture; performing a solids removal process on the mixture suitable for removing particles having a particle size of about 1.0 μm or larger to form a reduced solids mixture; and characterizing the silicon content of the hydrocarbonaceous sample using a detection method comprising inductively coupled plasma.

Embodiment 2

The method of Embodiment 1, wherein characterizing the silicon content of the hydrocarbonaceous sample comprises: separating a first fraction comprising a majority of the aromatic solvent and a second fraction comprising a majority of the silicon content from the reduced solids mixture; and characterizing the silicon content of the second fraction, the separating optionally comprising performing a separation based on distillation, evaporation, or a combination thereof.

Embodiment 3

The method of any of the above embodiments, wherein characterizing the silicon content of the hydrocarbonaceous sample comprises: characterizing the silicon content of the reduced solids mixture; and determining the silicon content of the hydrocarbonaceous sample based on at least one of the weight of the solvent in the mixture and the weight of the hydrocarbonaceous sample in the reduced solids mixture.

Embodiment 4

The method of any of the above embodiments, wherein the detection method comprises inductively coupled plasma atomic emission spectroscopy; or wherein the detection method comprises inductively coupled plasma mass spectrometry; or a combination thereof.

Embodiment 5

The method of any of the above embodiments, wherein performing a solids removal process on the mixture comprises filtration of the mixture.

Embodiment 6

The method of any of the above embodiments, wherein about 15 wt % or more of a silicon content in the mixture comprises inorganic silicon, or about 30 wt % or more, or about 45 wt % or more; or wherein about 10 wt % or less of a silicon content in the reduced solids mixture comprises inorganic silicon, or about 5 wt % or less; or a combination thereof.

Embodiment 7

The method of any of the above embodiments, wherein the mixture comprises about 20 wt % to about 80 wt % of the hydrocarbonaceous sample.

Embodiment 8

The method of any of the above embodiments, wherein the aromatic solvent comprises 50 wt % or more of 1-ring aromatic hydrocarbons; or wherein the aromatic solvent comprises at least one of benzene, toluene, and xylene; or a combination thereof.

Embodiment 9

The method of any of Embodiments 1-7, wherein the aromatic solvent comprises a naphtha boiling range fraction having an aromatics content of about 20 wt % or more (or about 25 wt % or more, or about 30 wt % or more).

Embodiment 10

The method of Embodiment 9, wherein the aromatics content of the naphtha boiling range fraction comprises aromatics containing heteroatoms, aromatics containing 2 or more aromatic rings, or a combination thereof or wherein the naphtha boiling range fraction comprises a 1-ring aromatic hydrocarbon content of about 20 wt % or more (or about 25 wt % or more, or about 30 wt % or more); or a combination thereof.

Embodiment 11

The method of any of the above embodiments, wherein the hydrocarbonaceous sample comprises a sample derived from a crude fraction, a refinery fraction, or a combination thereof, the refinery fraction optionally comprising a fraction that is at least in part bio-derived.

Embodiment 12

A system for characterizing a silicon content of a hydrocarbonaceous sample, comprising: a sample volume in fluid communication with a filter having a pore size of less than 1.0 μm; a nebulizer comprising a nebulizer inlet and a nebulizer outlet, the nebulizer inlet being in fluid communication with the permeate side of the filter; a plasma chamber comprising an inductively coupled argon plasma, the plasma chamber being in fluid communication with the nebulizer outlet; and an atomic emission spectrometer coupled to the plasma chamber.

Embodiment 13

The system of Embodiment 12, further comprising a boiling point separator comprising a separator inlet and a separator outlet, the separator inlet being in fluid communication with the sample volume, the separator outlet being in fluid communication with the filter, the sample volume being in indirect fluid communication with the filter via the boiling point separator, the boiling point separator optionally comprising at least one of a flash separator and a distillation column.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for determining the silicon content of a hydrocarbonaceous sample, comprising:
    mixing a hydrocarbonaceous sample with an aromatic solvent to form a mixture, the mixture comprising about 20 wt % to about 80 wt % of an aromatic solvent relative to a weight of the mixture;
    performing a solids removal process on the mixture suitable for removing particles having a particle size of about 1.0 µm or larger to form a reduced solids mixture; and
    characterizing the silicon content of the hydrocarbonaceous sample using a detection method comprising inductively coupled plasma, wherein characterizing the silicon content of the hydrocarbonaceous sample comprises:
    separating a first fraction comprising a majority of the aromatic solvent and a second fraction comprising a majority of the silicon content from the reduced solids mixture; and
    characterizing the silicon content of the second fraction.

2. The method of claim 1, wherein separating a first fraction comprising a majority of the aromatic solvent from the reduced solids mixture comprises performing a separation based on distillation, evaporation, or a combination thereof.

3. A method for determining the silicon content of a hydrocarbonaceous sample, comprising:
    mixing a hydrocarbonaceous sample with an aromatic solvent to form a mixture, the mixture comprising about 20 wt % to about 80 wt % of an aromatic solvent relative to a weight of the mixture;
    performing a solids removal process on the mixture suitable for removing particles having a particle size of about 1.0 µm or larger to form a reduced solids mixture; and
    characterizing the silicon content of the hydrocarbonaceous sample using a detection method comprising inductively coupled plasma, wherein characterizing the silicon content of the hydrocarbonaceous sample comprises:
    characterizing the silicon content of the reduced solids mixture; and
    determining the silicon content of the hydrocarbonaceous sample based on at least one of the weight of the solvent in the mixture and the weight of the hydrocarbonaceous sample in the reduced solids mixture.

4. The method of claim 1, wherein the detection method comprises inductively coupled plasma atomic emission spectroscopy.

5. The method of claim 1, wherein the detection method comprises inductively coupled plasma mass spectrometry.

6. The method of claim 1, wherein performing a solids removal process on the mixture comprises filtration of the mixture.

7. The method of claim 1, wherein about 15 wt % or more of a silicon content in the mixture comprises inorganic silicon, or about 30 wt % or more, or about 45 wt % or more.

8. The method of claim 1, wherein about 10 wt % or less of a silicon content in the reduced solids mixture comprises inorganic silicon, or about 5 wt % or less.

9. The method of claim 1, wherein the mixture comprises about 20 wt % to about 80 wt % of the hydrocarbonaceous sample.

10. The method of claim 1, wherein the aromatic solvent comprises 50 wt % or more of 1-ring aromatic hydrocarbons.

11. The method of claim 1, wherein the aromatic solvent comprises benzene, toluene, xylene, or a combination thereof.

12. The method of claim 1, wherein the aromatic solvent comprises a naphtha boiling range fraction having an aromatics content of about 20 wt % or more (or about 25 wt % or more, or about 30 wt % or more).

13. The method of claim 12, wherein the aromatics content of the naphtha boiling range fraction comprises aromatics containing heteroatoms, aromatics containing 2 or more aromatic rings, or a combination thereof.

14. The method of claim 12, wherein the naphtha boiling range fraction comprises a 1-ring aromatic hydrocarbon content of about 20 wt % or more (or about 25 wt % or more, or about 30 wt % or more).

15. The method of claim 1, wherein the hydrocarbonaceous sample comprises a sample derived from a crude fraction, a refinery fraction, or a combination thereof.

16. The method of claim 1, wherein the refinery fraction comprises a fraction that is at least in part bio-derived.

17. A system for characterizing a silicon content of a hydrocarbonaceous sample, comprising:
    a sample volume in fluid communication with a filter having a pore size of less than 1.0 µm;
    a nebulizer comprising a nebulizer inlet and a nebulizer outlet, the nebulizer inlet being in fluid communication with the permeate side of the filter;
    a plasma chamber comprising an inductively coupled argon plasma, the plasma chamber being in fluid communication with the nebulizer outlet;
    an atomic emission spectrometer coupled to the plasma chamber; and
    a boiling point separator comprising a separator inlet and a separator outlet, the separator inlet being in fluid communication with the sample volume, the separator outlet being in fluid communication with the filter, the sample volume being in indirect fluid communication with the filter via the boiling point separator, wherein the boiling point separator comprises at least one of a flash separator and a distillation column.

* * * * *